United States Patent
Wang

(10) Patent No.: US 11,006,885 B2
(45) Date of Patent: May 18, 2021

(54) APPARATUS FOR DETERMINING BLOOD PRESSURE

(71) Applicant: BOE TECHNOLOGY GROUP CO., LTD., Beijing (CN)

(72) Inventor: Guohe Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/563,612

(22) PCT Filed: Jun. 20, 2017

(86) PCT No.: PCT/CN2017/089150
§ 371 (c)(1),
(2) Date: Oct. 1, 2017

(87) PCT Pub. No.: WO2018/040680
PCT Pub. Date: Mar. 8, 2018

(65) Prior Publication Data
US 2019/0175042 A1   Jun. 13, 2019

(30) Foreign Application Priority Data
Sep. 5, 2016 (CN) .......................... 201610801498.0

(51) Int. Cl.
*A61B 5/00* (2006.01)
*A61B 5/341* (2021.01)
(Continued)

(52) U.S. Cl.
CPC ............ *A61B 5/341* (2021.01); *A61B 5/0006* (2013.01); *A61B 5/0245* (2013.01);
(Continued)

(58) Field of Classification Search
CPC ....... A61B 5/04001; A61B 5/02; A61B 5/021; A61B 5/02108; A61B 5/02125; A61B 5/04011
See application file for complete search history.

(56) References Cited

U.S. PATENT DOCUMENTS 6,647,287 B1 * 11/2003 Peel, III ............. A61B 5/02125
600/485
9,706,964 B2 * 7/2017 Ferber .................. A61B 5/7278
(Continued)

FOREIGN PATENT DOCUMENTS

CN       101264011 A      9/2008
CN       102397064 A      4/2012
(Continued)

OTHER PUBLICATIONS

International Search Report and Written Opinion in PCT/CN2017/089150 dated Aug. 23, 2017.
(Continued)

*Primary Examiner* — Jennifer Pitrak McDonald
*Assistant Examiner* — Sana Sahand
(74) *Attorney, Agent, or Firm* — Syncoda LLC; Feng Ma

(57) ABSTRACT

A method for determining a blood pressure of a user includes: collecting an electrocardiography (ECG) signal and a pulse wave signal from the user; extracting characteristic parameters of the user from the ECG signal and the pulse wave signal; establishing a characteristic vector of the user based on personal information of the user and the characteristic parameters of the user; and determining the blood pressure of the user based on the characteristic vector of the user and a characteristic-vector-and-blood-pressure relational model. A blood pressure determining apparatus based on the method disclosed herein is also provided, which includes an acquisition portion, a characteristic parameter determination portion, a characteristic vector
(Continued)

determination portion, and a blood pressure determination portion.

14 Claims, 9 Drawing Sheets

(51) Int. Cl.
*A61B 5/0245* (2006.01)
*A61B 5/021* (2006.01)
*A61B 5/318* (2021.01)
*A61B 5/352* (2021.01)

(52) U.S. Cl.
CPC ...... *A61B 5/02108* (2013.01); *A61B 5/02125* (2013.01); *A61B 5/318* (2021.01); *A61B 5/352* (2021.01); *A61B 5/6801* (2013.01); *A61B 5/6898* (2013.01); *A61B 5/7278* (2013.01)

(56) References Cited

U.S. PATENT DOCUMENTS

| | | | |
|---|---|---|---|
| 10,045,700 B2* | 8/2018 | Noh | A61B 5/1102 |
| 2006/0085137 A1* | 4/2006 | Bartkowiak | A61B 5/14532 |
| | | | 702/19 |
| 2010/0081946 A1 | 4/2010 | Garudadri et al. | |
| 2012/0078123 A1 | 3/2012 | Futatsuyama et al. | |
| 2015/0038860 A1* | 2/2015 | Fonte | A61B 6/50 |
| | | | 600/505 |
| 2017/0071484 A1* | 3/2017 | Strachan | A61B 5/7264 |
| 2017/0215749 A1* | 8/2017 | Zhuo | A61B 5/02055 |
| 2017/0286627 A1* | 10/2017 | Barhak | G06N 5/003 |
| 2018/0078156 A1* | 3/2018 | Chen | A61B 5/02125 |
| 2018/0192900 A1* | 7/2018 | Wei | A61B 5/0225 |
| 2019/0307337 A1* | 10/2019 | Little | A61B 5/04085 |

FOREIGN PATENT DOCUMENTS

| | | | |
|---|---|---|---|
| CN | 102488503 B | * | 2/2014 |
| CN | 105147269 A | | 12/2015 |
| CN | 105725999 A | | 7/2016 |
| CN | 105748051 A | | 7/2016 |
| WO | WO-2013056319 A1 | * 4/2013 | ......... A61B 5/02108 |

OTHER PUBLICATIONS

2nd Office Action in CN201610801498.0 dated Oct. 30, 2019.
Jung Yi Kim et al. "Comparative study on artificial neural network with Multiple regressions for continuous estimation of blood pressure", Engineering in Medicine and Biology 27th Annual Conference, vol. 2005, pp. 6942-6945, 2005-123-1.
Yang Song Xiao et al., "SVM-based regression continuous blood pressure measurement method", Journal of Jilin University, May 31, 2016, vol. 34, No. 3, pp. 384-389.
1st Office Action in CN201610801498.0 dated Jun. 4, 2019.
4th Office Action in CN201610801498.0 dated Jun. 10, 2020.

* cited by examiner

APPARATUS FOR DETERMINING BLOOD PRESSURE

CROSS-REFERENCE TO RELATED APPLICATION

The present application claims priority to Chinese Patent Application No. 201610801498.0 filed on Sep. 5, 2016, the disclosure of which is hereby incorporated by reference in its entirety.

TECHNICAL FIELD

The present disclosure relates generally to a field of health monitoring technologies, and more specifically to a method and an apparatus for determining blood pressure.

BACKGROUND

Hypertension is a common cardiovascular disease; worldwide the number of hypertension patients is large and is still on the rise. An accurate measurement of the blood pressure in an individual is very important for the diagnosis, management, and treatment of hypertension in the same individual.

Traditional blood pressure measurement technologies can include an invasive approach and a non-invasive approach. An invasive measurement typically involves inserting a catheter into an artery and directly measuring the arterial pressure through a transducer. This approach usually causes trauma, is commonly expensive, and is thus not suitable for daily measurement in a household setting.

A non-invasive measurement typically involves cuff inflation and deflation and commonly uses Korotkoff sound or vibration waves to measure blood pressure. The inflation and deflation is not only easy to cause vascular and tissue damage in places wearing a cuff, and the measurement typically requires a certain period of time, and is unable to achieve a continuous observation of the blood pressure.

A new blood pressure measurement technology based on pulse waves, especially based on photoplethysmography (PPG), has been develop in order to realize a cuff-less continuous measurement of blood pressure. This technology is based on a principle that the pulse transit time (PTT) of an individual is correlated to the blood pressure, yet due to the inter-individual difference in the model correlating PTT with the blood pressure, a calibration is needed before use for each individual person, which causes an inconvenience during use.

SUMMARY

The present disclosure provides a method and an apparatus for determining blood pressure, which can address the issues associated with current blood pressure measuring technologies, such as the inconvenience due to the need for calibration before use for each individual person.

In a first aspect, a method for determining a blood pressure of a user is disclosed. The method includes the following steps:

collecting an electrocardiography (ECG) signal and a pulse wave signal from the user;

extracting characteristic parameters of the user from the ECG signal and the pulse wave signal;

establishing a characteristic vector of the user based on personal information of the user and the characteristic parameters of the user; and determining the blood pressure of the user based on the characteristic vector of the user and a characteristic-vector-and-blood-pressure relational model.

Prior to the step of collecting an electrocardiography (ECG) signal and a pulse wave signal from the user, the method can further include a step of:

establishing the characteristic-vector-and-blood-pressure relational model by means of a sample dataset;

Herein the sample dataset comprises a plurality of records. Each record corresponds to one of a plurality of sample individuals and comprises pre-determined characteristic parameters at each of a plurality of time intervals, a pre-determined blood pressure, and pre-determined personal information of the one of the plurality of sample individuals.

In the method as described above, the step of establishing the characteristic-vector-and-blood-pressure relational model by means of a sample dataset can include the following sub-steps:

building the characteristic-vector-and-blood-pressure relational model over a first subset of the sample dataset, wherein the first subset comprises records corresponding to a first sub-population of the sample individuals, comprising:

establishing a characteristic vector of each of the first sub-population of the sample individuals based on the pre-determined personal information and the pre-determined characteristic parameters corresponding thereto; and determining the characteristic-vector-and-blood-pressure relational model based on a formula:

$$y = \sum_{i=1}^{l} (\alpha_i - \alpha_i^*) K(x, x_i) + b;$$

where y is the blood pressure, l is a number of characteristic vectors of the first sub-population of the sample individuals, $K(x, x_i)$ is a kernel function, x is a characteristic vector of a user, $x_i$ is a characteristic vector of the first sub-population of the sample individuals, and $\alpha_i$, $\alpha_i^*$, b are optimal coefficients after training.

According to some embodiments of the method, in the sub-step of determining the characteristic-vector-and-blood-pressure relational model based on a formula $$y = \sum_{i=1}^{l} (\alpha_i - \alpha_i^*) K(x, x_i) + b,$$

the training is carried out via support vector machine (SVM).

In the method as described above, the blood pressure can be a diastolic blood pressure or a systolic blood pressure.

Furthermore, the kernel function can be a polynomial function or a Gauss function.

In the method as described above, the step of establishing the characteristic-vector-and-blood-pressure relational model by means of a sample dataset can further include the sub-step of:

testing the characteristic-vector-and-blood-pressure relational model over a second subset of the sample dataset, wherein the second subset is different from the first subset and comprises records corresponding to a second sub-population of the sample individuals.

Herein the sub-step of testing the characteristic-vector-and-blood-pressure relational model over a second subset of the sample dataset comprises:

obtaining a calculated blood pressure of the second sub-population of the sample individuals based on the characteristic-vector-and-blood-pressure relational model and the characteristic vector of the second sub-population of the sample individuals; and determining whether a difference between the calculated blood pressure and a pre-determined blood pressure of the second sub-population of the sample individuals satisfies a standard.

Herein the standard is pre-selected.

According to some embodiments of the method, after the sub-step of testing the characteristic-vector-and-blood-pressure relational model over a second subset of the sample dataset, the step of establishing the characteristic-vector-and-blood-pressure relational model by means of a sample dataset further includes a sub-step of:

re-determining the characteristic-vector-and-blood-pressure relational model, if the difference between the calculated blood pressure and the pre-determined blood pressure of the second sub-population of the sample individuals is determined not to satisfy the standard, until the standard is met.

In the method as described above, the standard can include at least one of within ±5 mmHg for an average of the difference, or <12 mmHg of a standard deviation.

In any of the embodiments of the method as mentioned above, the characteristic parameters comprise a heart rate, a pulse wave transmit time, a pulse wave rise time, a pulse wave fall time, and a pulse wave peak value and a pulse wave trough value of two adjacent repeat cycles.

Further in any of the embodiments of the method as mentioned above, the personal information of the user can comprise gender, age, height, and weight of the user.

In a second aspect, the present disclosure further provides an apparatus for determining a blood pressure of a user. The apparatus includes an acquisition portion, a characteristic parameter determination portion, a characteristic vector determination portion, and a blood pressure determination portion.

The acquisition portion is configured to collect a pulse wave signal and an ECG signal from the user; the characteristic parameter determination portion is configured to extract characteristic parameters of the user based on the pulse wave signal and the ECG signal collected by the acquisition portion; the characteristic vector determination portion is configured to establish a characteristic vector of the user based on the characteristic parameters of the user extracted by the characteristic parameter determination portion and personal information of the user; and the blood pressure determination portion is configured to determine the blood pressure of the user based on the characteristic vector of the user established by the characteristic vector determination portion and a characteristic-vector-and-blood-pressure relational model.

According to some embodiments of the apparatus, the acquisition portion and the characteristic parameter determination portion are arranged in an acquisition device, the characteristic vector determination portion and the blood pressure determination portion are arranged in a computing device, and the acquisition device is configured to send the characteristic parameters of the user to the computing device.

In the apparatus as described above, the acquisition device can comprise a wearable smart device; and the computing device can include one of a smart phone, a computer, or a remote server.

In the apparatus as described above, the acquisition device can be configured to send the characteristic parameters of the user to the computing device via a wireless communication, and the wireless communication can be selected from one of a cellular communication, a Bluetooth communication, and a Wi-Fi communication.

It is noted that the acquisition device can also be configured to send the characteristic parameters of the user to the computing device via a wired communication.

According to some embodiments, the apparatus can further include a model determination portion, which is configured to determine a characteristic-vector-and-blood-pressure relational model based on the characteristic vector and corresponding blood pressure of a first sub-population of sample individuals.

In these aforementioned embodiments of the apparatus, the acquisition portion is further configured to measure a pulse wave signal, an ECG signal, and a blood pressure of each of a plurality of sample individuals at each of a plurality of time intervals; and the characteristic vector determination portion is further configured, after extracting characteristic parameters of each sample individual at each time interval from the ECG signal and the pulse wave signal thereof, to establish a characteristic vector of the each sample individual based on the characteristic parameters and pre-determined personal information of the each sample individual.

According to some embodiments, the apparatus can further includes a model testing portion. The model testing portion is configured, after the characteristic-vector-and-blood-pressure relational model is determined, to obtain a calculated blood pressure of a second sub-population of the sample individuals based on the characteristic-vector-and-blood-pressure relational model and the characteristic vector of the second sub-population of the sample individuals; and if a difference between the calculated blood pressure and the measured blood pressure of the second sub-population of the sample individuals does not satisfy a standard, to re-determine the characteristic-vector-and-blood-pressure relational model until the standard is met.

In the method and the apparatus for determining a blood pressure of a user as disclosed herein, the blood pressure of a user can be determined based on the characteristic vector of the user and the pre-established characteristic-vector-and-blood-pressure relational model, realizing a cuff-less measurement of the blood pressure.

Additionally, the characteristic vector of the user includes the personal information of the user and the characteristic parameters of the user that are determined based on the ECG signal and the pulse wave signal of the user. As such, during the process of blood pressure measurement, there is no need to calibrate for each individual person, bringing about convenience for use.

Furthermore, because the blood pressure of the user is determined based on both the ECG signal and the pulse wave signal, the measurement result is thus more accurate than the result obtained from a conventional measurement approach, where only the pulse wave signal is based to obtain the blood pressure.

BRIEF DESCRIPTION OF DRAWINGS

To more clearly illustrate some of the embodiments provided by the present disclosure, the following is a brief description of the drawings. The drawings in the following descriptions are only illustrative of some embodiments. For those of ordinary skill in the art, other drawings of other embodiments can become apparent based on these drawings.

DETAILED DESCRIPTION

In the following, with reference to the drawings of the embodiments disclosed herein, the technical solutions of the embodiments of the invention will be described in a clear and fully understandable way. It is noted that the described embodiments are merely a portion but not all of the embodiments of the invention. Based on the described embodiments of the invention, those ordinarily skilled in the art can obtain other embodiment(s), which come(s) within the scope sought for protection by the invention.

In order to address the issues associated with current blood pressure measuring technologies, such as the inconvenience due to the need for calibration before use for each individual person, the present disclosure provides a method and an apparatus for determining a blood pressure of a user.

In a first aspect, a method for determining a blood pressure of a user is disclosed herein, whose description is provided below with reference to the figures.

Figure 1:
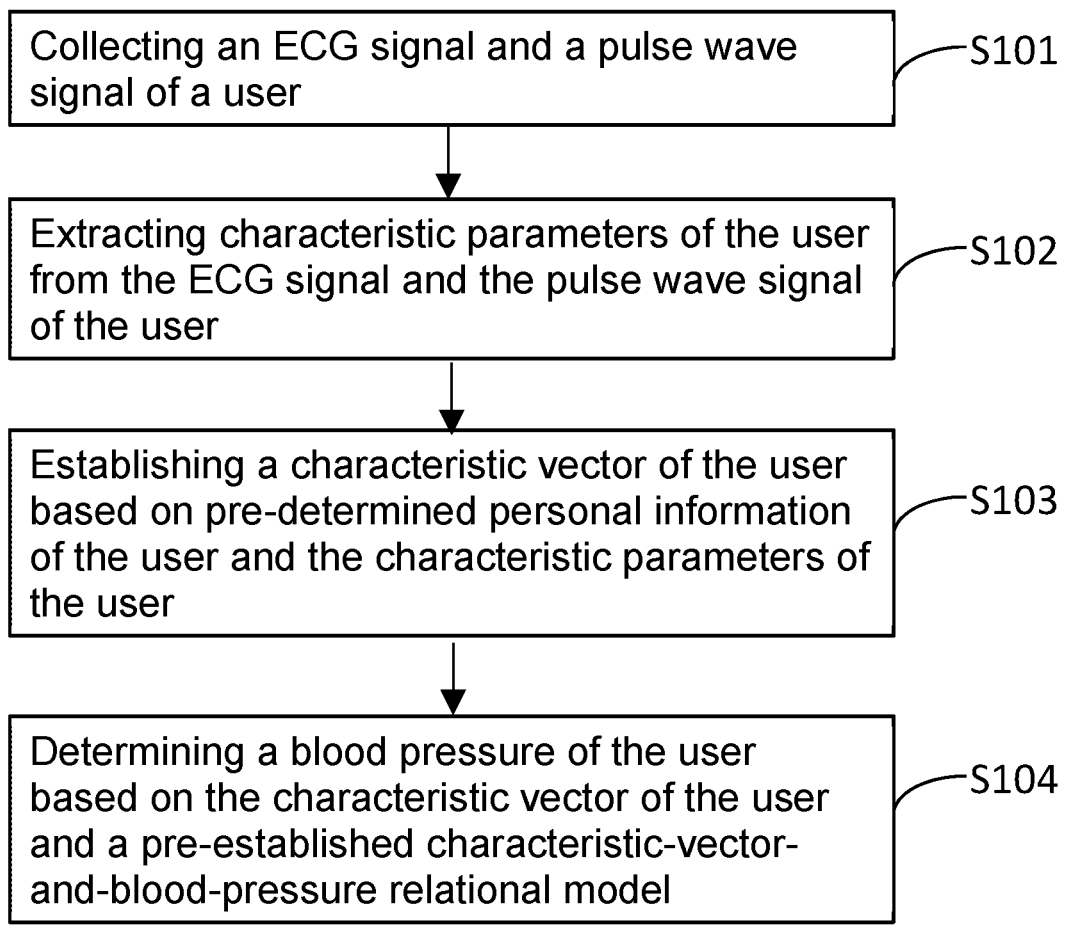
FIG. 1 shows a flowchart of a method for determining a blood pressure of a user according to some embodiments of the present disclosure.

FIG. 1 shows a flowchart of a method for determining a blood pressure of a user of a user according to some embodiments of the present disclosure. As shown in FIG. 1, the method comprises the following steps:

S101: collecting an electrocardiography (ECG) signal and a pulse wave signal of the user;

S102: extracting characteristic parameters of the user from the ECG signal and the pulse wave signal of the user;

S103: establishing a characteristic vector of the user based on pre-determined personal information of the user and the characteristic parameters of the user;

S104: determining the blood pressure of the user based on the characteristic vector of the user and a pre-established characteristic-vector-and-blood-pressure relational model (i.e., relational model correlating the characteristic vector and the blood pressure).

In the above mentioned method for determining a blood pressure of a user, the blood pressure of the user can be determined based on the characteristic vector of the user and a pre-established characteristic-vector-and-blood-pressure relational model, realizing a cuff-less measurement of the blood pressure.

Additionally, the characteristic vector of the user includes the personal information of the user and the characteristic parameters of the user that are determined based on the ECG signal and the pulse wave signal of the user. As such, during the process of blood pressure measurement, there is no need to calibrate for each individual person, bringing about convenience for use.

Furthermore, because the blood pressure of the user is determined based on both the ECG signal and the pulse wave signal, the measurement result is thus more accurate than the result obtained from a conventional measurement approach, where only the pulse wave signal is based to obtain the blood pressure.

During an implementation of step S101, the pulse wave signal of the user can be obtained by a pulse wave signal collection device, such as a photoplethysmography (PPG) signal collection device (the corresponding signal is also called PPG signal); and the ECG signal of the user can be obtained through an electrode of an electrocardiography signal collection device, which together can realize a cuff-less measurement of the blood pressure.

In practice, the pulse wave signal collection device can be shaped as, or embedded in, a bracelet, and the electrocardiography signal collection device can be separately shaped as, or embedded in, a small-size wearable device. Alternatively, the pulse wave signal collection device and the electrocardiography signal collection device can be integrated together into a small wearable device, such as a bracelet. By means of a mobile application, a real-time blood pressure measurement can be realized.

During an implementation, the collection of the ECG signal and the pulse wave signal of the user in step S101 and the extraction of the characteristic parameters of the user from the ECG signal and the pulse wave signal of the user in step S102 can be carried out by an acquisition device having a data processor.

The acquisition of the personal information of the user, and the establishment of the characteristic vector of the user based on the personal information of the user and the characteristic parameters of the user in step S103, and the determination of the blood pressure of the user based on the characteristic vector of the user and the pre-established characteristic-vector-and-blood-pressure relational model in step S104 can be carried out by a smart terminal (e.g., a smart phone, a personal computer, etc.)

If the collection device(s) has sufficiently high data transmission power, the collection device(s) can also transmit the ECG signal and the pulse wave signal of the user to a smart terminal, and the smart terminal can carry out all data processing work.

In a preferred embodiment, the smart terminal is a smart phone. The collection device(s) send the characteristic parameters of the user to the smart phone via a wireless transmission such as Bluetooth, and the blood pressure of the user can be calculated in the smart phone. As such, a user can monitor his/her blood pressure via a smart phone at any time, realizing a real-time monitoring of the blood pressure in a quite convenient manner.

In the method for determining a blood pressure of a user as described above, the step of extracting characteristic parameters of the user from the ECG signal and the pulse wave signal of the user (i.e. step S102) can specifically comprise:

Extracting the characteristic parameters of the user from the ECG signal and the pulse wave signal of the user, wherein the characteristic parameters of the user comprise a heart rate, a pulse wave transmit time, a pulse wave rise time, a pulse wave fall time, and a pulse wave peak value and a pulse wave trough value of two adjacent repeat cycles.

Herein the pre-determined personal information of the user can include gender, age, height, and weight, etc. of the user.

In the method for determining a blood pressure of a user as described above, by calculating the blood pressure through extracting multiple characteristic parameters of the user, an accuracy of the blood pressure that is calculated thereby can be improved. In addition, the combination of the personal information in the calculation of the blood pressure allows the method to be applied in various populations, thus negating the requirement for calibration for each individual person.

During an implementation of step S102, the peaks of the ECG signal and the characteristic points of the pulse wave signal need to be recognized and detected first.

Figure 2A:
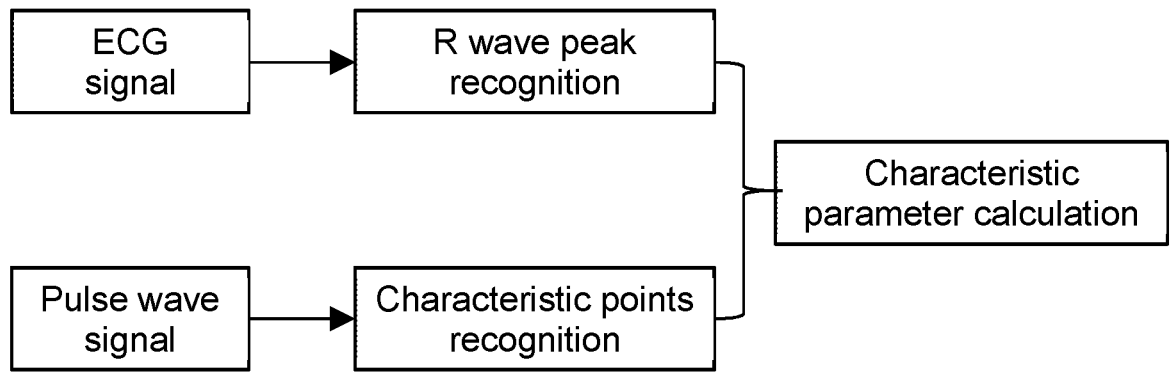
FIG. 2A is a flowchart of extracting the characteristic parameters from the ECG signal and the pulse wave signal of the user according to some embodiments of the present disclosure.

FIG. 2A is a flowchart of extracting the characteristic parameters from the ECG signal and the pulse wave signal of the user according to some embodiments of the present disclosure.

As shown in FIG. 2A, in the embodiments, the process of extracting the characteristic parameters comprises: performing a R wave peak recognition to the ECG signal and a characteristic point recognition to the pulse wave signal, then based on the recognition results, the characteristic parameters of the user are then calculated.

Figure 2B:
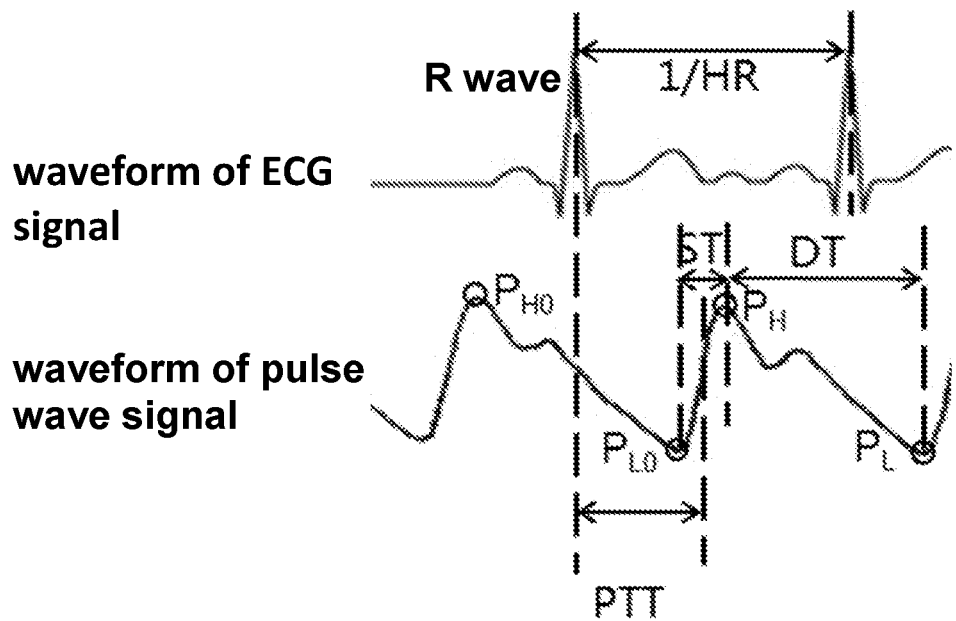
FIG. 2B illustrates a schematic diagram of determining characteristic parameters based on an electrocardiography (ECG) signal and a pulse wave signal according to the embodiments as shown in FIG. 2A.
Figure 3:
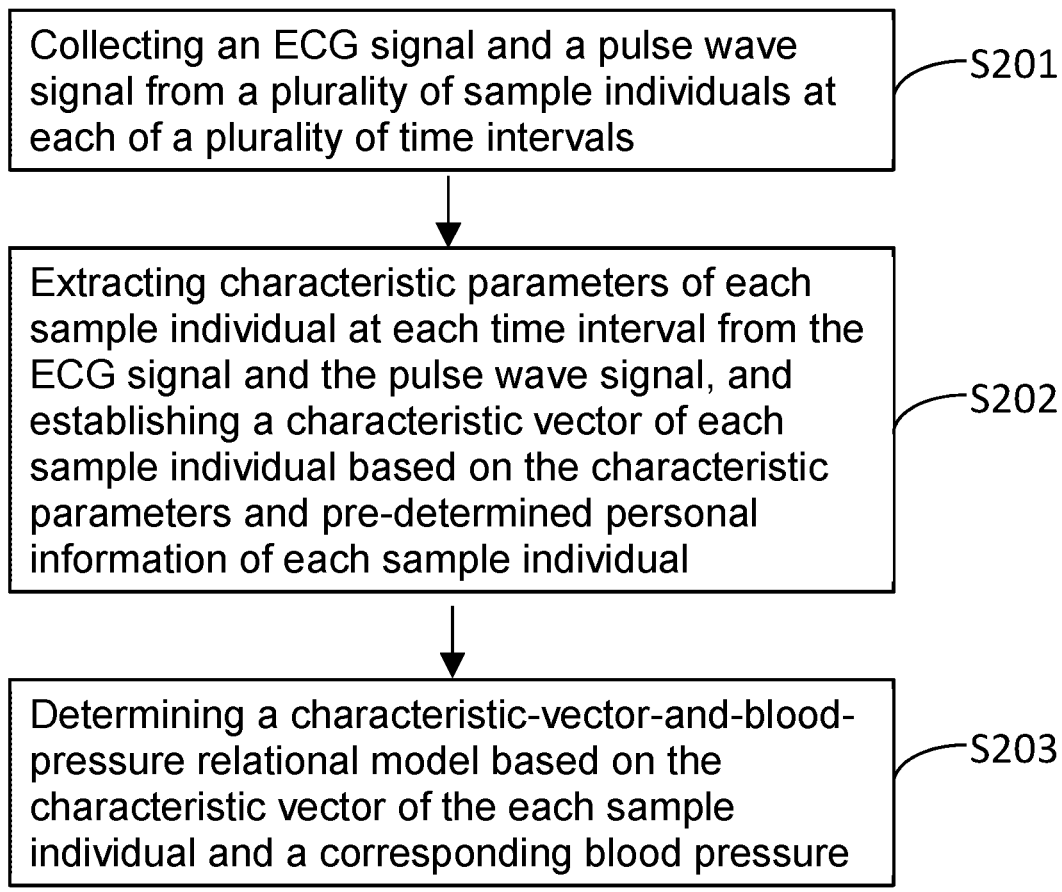
FIG. 3 shows a flowchart of determining a characteristic-vector-and-blood-pressure relational model in the method for determining a blood pressure of a user according to some embodiments of the present disclosure.
Figure 4:
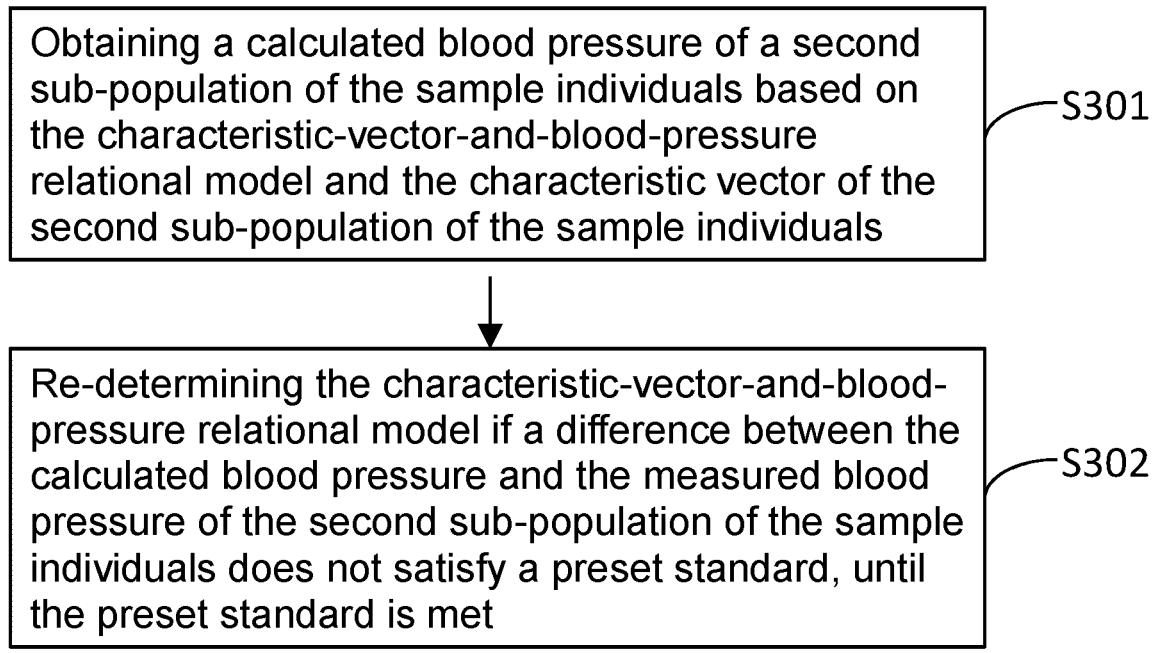
FIG. 4 shows a flowchart of testing the relational model in the method for determining a blood pressure of a user according to some embodiments of the present disclosure.

FIG. 2B illustrates a schematic diagram of determining characteristic parameters of the user based on the ECG signal and the pulse wave signal according to the embodiments as shown in FIG. 2A.

As shown in FIG. 2B, the ECG signal is typically a R wave. By recognizing the waveforms of the ECG signal and the pulse wave signal, the characteristic parameters of the user can be obtained. The heart rate can be obtained by taking a reciprocal of the time interval of a minimum repeat cycle in the waveform of the ECG signal. In the illustrating example as shown in FIG. 2B, by calculating a distance between the two adjacent wave peaks in the waveform of the ECG signal (shown as 1/HR in FIG. 2B), the heart rate (HR) can be obtained.

The pulse wave transit time (shown as PTT in FIG. 2B) is the time interval from a peak of the wave to the point in a rising segment of the wave having a maximum slope. The pulse wave rise time (shown as ST in FIG. 2B) is the time interval from a trough rising to a peak of a minimum pulse repeat cycle. The pulse wave fall time (shown as DT in FIG. 2B) is the time interval from a peak falling to a trough of a minimum pulse repeat cycle.

The peak values and the trough values of the pulse wave in two adjacent repeat cycles are the peak value $P_{H0}$ and the trough value $P_{L0}$ in the previous repeat cycle, and the peak value $P_H$ and the trough value $P_L$ in the current repeat cycle.

It is noted that characteristic parameters other than those mentioned above can also be selected, and that the characteristic parameters can also include other parameters. It is also noted that the personal information can also include other information. There are no limitations herein.

Specifically, in the method for determining a blood pressure of a user, the aforementioned characteristic-vector-and-blood-pressure relational model can be determined by carrying out the following sub-steps:

S201: collecting an ECG signal and a pulse wave signal from each of a plurality of sample individuals at each of a plurality of time intervals;

S202: extracting characteristic parameters of each sample individual at each time interval from the ECG signal and the pulse wave signal of the each sample individual, and establishing a characteristic vector of the each sample individual based on the characteristic parameters and pre-determined personal information of the each sample individual;

S203: determining a characteristic-vector-and-blood-pressure relational model based on the characteristic vector of the each sample individual and a corresponding blood pressure.

In the method as described above, the blood pressure that is measured or collected can be a diastolic blood pressure or a systolic blood pressure. Both the diastolic blood pressure and the systolic blood pressure can correspond to a same characteristic-vector-and-blood-pressure relational model, yet the diastolic blood pressure and the systolic blood pressure correspond to different optimal coefficient for each parameter.

As such, the characteristic-vector-and-blood-pressure relational model that is established based on the formula $$y = \sum_{i=1}^{l} (\alpha_i - \alpha_i^*) K(x, x_i) + b$$

shall correspond to the selected blood pressure (i.e. the diastolic blood pressure or the systolic blood pressure), with different optimal coefficient for each parameter, and thus the blood pressure that is determined based on the characteristic vector of the user and a characteristic-vector-and-blood-pressure relational model shall also correspond to the selected blood pressure, and cannot be mixed.

For example, if the formula $$y = \sum_{i=1}^{l} (\alpha_i - \alpha_i^*) K(x, x_i) + b$$

is established on basis of the diastolic blood pressure, only a diastolic blood pressure for the user can be determined, and the use of the formula established on basis of the systolic blood pressure will give a incorrect result for the blood pressure of the user.

In an implementation of the method, depending on whether the blood pressure is a diastolic blood pressure or a systolic blood pressure, sub-steps S201-S203 can be respectively executed to determine the correspondence relationship and the optimal coefficients of each parameter corresponding respectively to the diastolic blood pressure and the systolic blood pressure. It is noted that when respectively executing sub-step S201, a pulse wave signal, an ECG signal, and a corresponding blood pressure at a same moment need to be collected.

In sub-step S201, the blood pressure of a sample individual at a time interval can be measured by a high-precision blood-pressure meter (e.g. a mercury sphygmomanometer) in the arm or by an invasive blood pressure measurement. At the same time, the pulse wave signals and ECG signal of said sample individual at said time interval can be obtained by one or more collection devices.

In some embodiments, it can be configured that the blood pressure is measured by a high-precision blood-pressure meter from one arm, while the pulse wave signal is obtained from the other arm, to thereby obtain the pulse wave signal, the ECG signal, and the blood pressure of a sample individual at a time interval, which are then combined with the personal information of the sample individual to thereby acquire a group of data associated with said sample individual at said time interval.

Because a different blood pressure and a corresponding characteristic vector for each sample individual are needed for establishing the characteristic-vector-and-blood-pressure relational model, a blood pressure and its corresponding pulse wave signal and ECG signal for a same sample individual at different time intervals need to be collected to thereby increase the accuracy of the characteristic-vector-and-blood-pressure relational model.

The characteristic-vector-and-blood-pressure relational model can be trained by a support vector machine (SVM).

In the method as described above, sub-step S203 can specifically comprise:

Determining the characteristic-vector-and-blood-pressure relational model based on the formula:

$$y = \sum_{i=1}^{l} (\alpha_i - \alpha_i^*)K(x, x_i) + b$$

where y is the blood pressure, l is the number of the characteristic vector of a sub-population of the sample individuals, $K(x,x_i)$ is the kernel function (e.g. a polynomial or Gauss function), x is the characteristic vector of a user, $x_i$ is the characteristic vector of the sub-population of the sample individuals, $\alpha_i$, $\alpha_i^*$, b are the optimal coefficients for each parameter after training. If the diastolic pressure is measured, the optimal coefficients are the optimal coefficients corresponding to the diastolic pressure; if the systolic pressure is measured, the optimal coefficients are the optimal coefficients corresponding to the systolic pressure.

It is noted that the above formula can be applied to calculate the diastolic pressure or the systolic pressure, yet the optimal coefficients corresponding to the diastolic pressure are different from the optimal coefficients corresponding to the systolic pressure. If the diastolic pressure is to be calculated, the optimal coefficients corresponding to the diastolic pressure shall be used; if the systolic pressure is to be calculated, the optimal coefficients corresponding to the systolic pressure shall be used.

In the method, the establishing a characteristic vector of the each sample individual in sub-step S202 can further comprise:

Performing a preprocessing (which can include normalization and removal of erroneous data) to the characteristic parameters, the blood pressure, and the personal information of each sample individual obtained at different time intervals; and Establishing a characteristic vector of the each sample individual at each time interval based on the preprocessed characteristic parameters, blood pressure, and personal information of the each sample individual at different time intervals.

Herein by normalization and removal of erroneous data, the accuracy of the characteristic-vector-and-blood-pressure relational model can be further improved.

After determining the characteristic-vector-and-blood-pressure relational model, the method can further comprise:

S301: obtaining a calculated blood pressure of a second sub-population of the sample individuals based on the characteristic-vector-and-blood-pressure relational model and the characteristic vector of the second sub-population of the sample individuals;

S302: re-determining the characteristic-vector-and-blood-pressure relational model if a difference between the calculated blood pressure and the measured blood pressure of the second sub-population of the sample individuals does not satisfy a preset standard, until the preset standard is met.

Figure 5A:
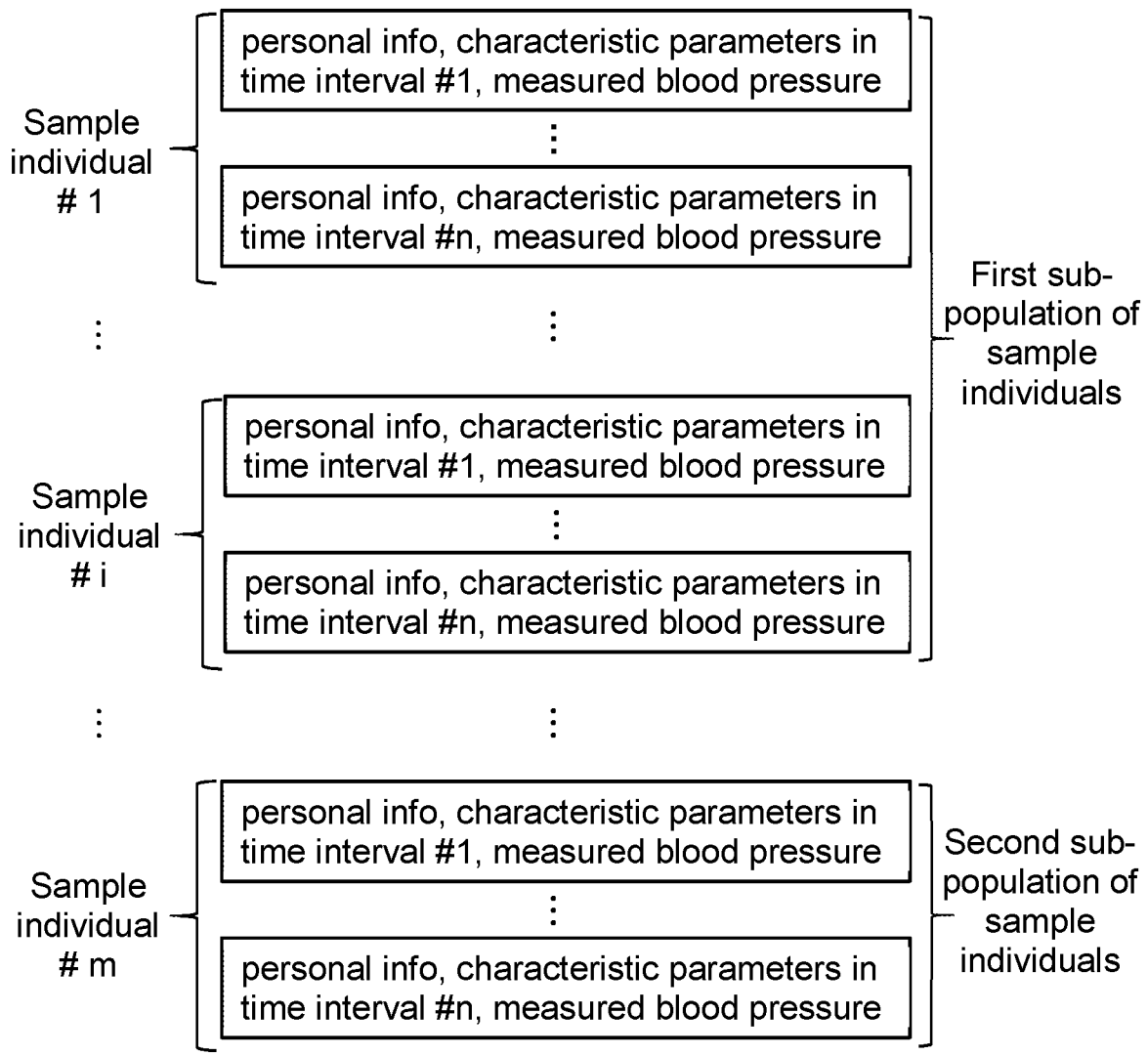
FIG. 5A illustrates a schematic diagram of data allocation for a first sub-population and a second sub-population of the sample individuals in the method for determining a blood pressure of a user according to some embodiments of the present disclosure.

During implementation of sub-step S201, the plurality of sample individuals can be divided into a first sub-population of the sample individuals, whose data are used as sample data, and a second sub-population of the sample individuals, whose data are used as testing data (illustrated in FIG. 5A). In order to ensure an accuracy of the correspondence relationship, a relatively large number of the sample individuals are needed.

The first sub-population of the sample individuals are for the determination of the characteristic-vector-and-blood-pressure relational model, whereas the second sub-population of the sample individuals are for the testing of the optimal coefficients of each parameter in the relational model of the characteristic vector and the blood pressure that have been determined.

Similarly, in order to ensure an accuracy of the characteristic-vector-and-blood-pressure relational model and the optimal coefficient of each parameter, a relatively large number of the sample individuals for the first sub-population of the sample individuals and for the second sub-population of the sample individuals are selected. Herein there are no limitations to the number of the sample individuals, the number of the first sub-population of the sample individuals, and the number of the second sub-population of the sample individuals.

The preset standard in the above mentioned sub-step S302 can be set as within ±5 mmHg for an average of the difference, or <12 mmHg of the standard deviation. The accuracy of the relational model can be determined by an average or a standard deviation of the difference between the calculated blood pressure based on the second sub-population of the sample individuals and the measured blood pressure.

Specifically, in sub-step S301, the characteristic vector of each of the second sub-population of the sample individuals can be used to replace $x_i$ in the relational model for the calculation, and the calculated blood pressure and the measured blood pressure of each of the second sub-population of the sample individuals can be compared. If the comparison result meets a preset standard, the optimal coefficients for each parameter meets the requirement, otherwise, the characteristic-vector-and-blood-pressure relational model needs to be re-determined, until the preset standard is met.

Figure 5B:
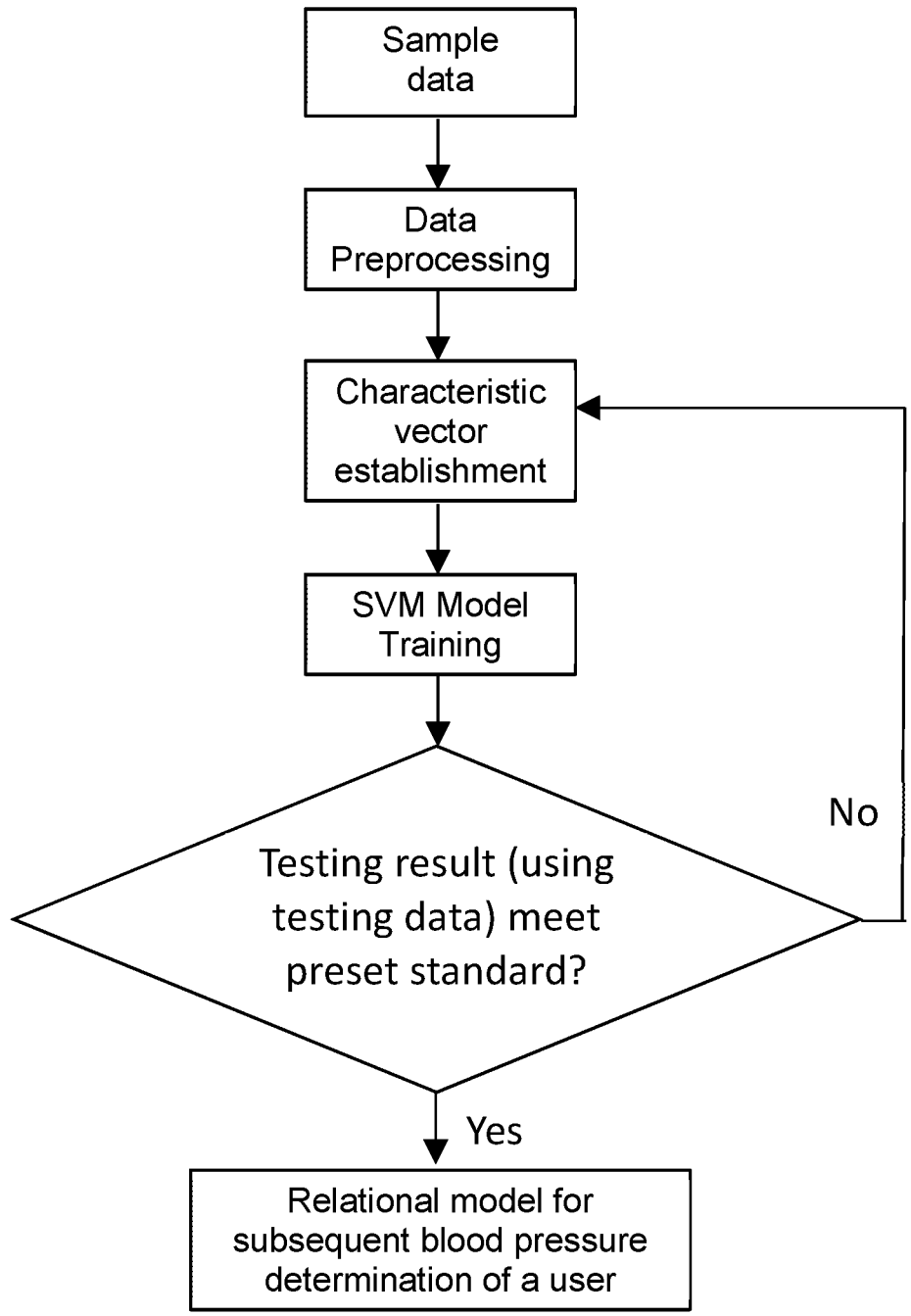
FIG. 5B is a flowchart of establishing the characteristic-vector-and-blood-pressure relational model in the method for determining a blood pressure of a user according to some embodiments of the present disclosure.

As one illustrating example, FIG. 5B is a flowchart of establishing the characteristic-vector-and-blood-pressure relational model according to some embodiments of the present disclosure.

First, measurements data of a blood pressure (preferably measured by a high-precision blood-pressure meter), an ECG signal and a pulse wave signal are collected from each of a plurality of sample individuals in each of a plurality of time intervals. The measurement data are combined with the personal information of each sample individual to thereby form a complete record for each sample individual. The complete record for each sample individual are combined together to form a sample dataset, which is divided into two portions.

A first sub-population of the sample datasets, which include measurement data and personal information of a first sub-population of the sample individuals, will be used as a sample data, whereas a second sub-population of the sample datasets, which include measurement data and personal information of a second sub-population of the sample individuals, will be used as a testing data.

Then after data preprocessing (such normalization and removal of erroneous data), characteristic vector establishment, and SVM training over the sample data of the sample sub-population (i.e. the first sub-population), a characteristic-vector-and-blood-pressure relational model can be established.

Next, the characteristic-vector-and-blood-pressure relational model that has been obtained from the sample data is tested using the testing data of the testing sub-population (i.e., the second sub-population).

If a testing result meets a preset standard (e.g., difference between a calculated blood pressure and a measured blood pressure is within a certain range), the characteristic-vector-and-blood-pressure relational model that has been obtained from the sample data will be output and used as the characteristic-vector-and-blood-pressure relational model for subsequent determination of a blood pressure of a user.

If the testing result does not meet the preset standard, then the characteristic vector establishment and SVM training will be performed again to thereby re-determine a second characteristic-vector-and-blood-pressure relational model.

Such process is continued until finally the preset standard is met, and the characteristic-vector-and-blood-pressure relational model that has been obtained in the last round will be used as the relational model for the subsequent determination of a blood pressure of a user.

It is noted that the above steps for determining the characteristic-vector-and-blood-pressure relational model as illustrated in FIG. 5B represents only one embodiment, and other embodiments are also possible. There are no limitations herein.

In a second aspect, the present disclosure further provides an apparatus for determining a blood pressure of a user. The apparatus is designed based on a same principle as the method for determining a blood pressure of a user as described above.

Figure 6A:
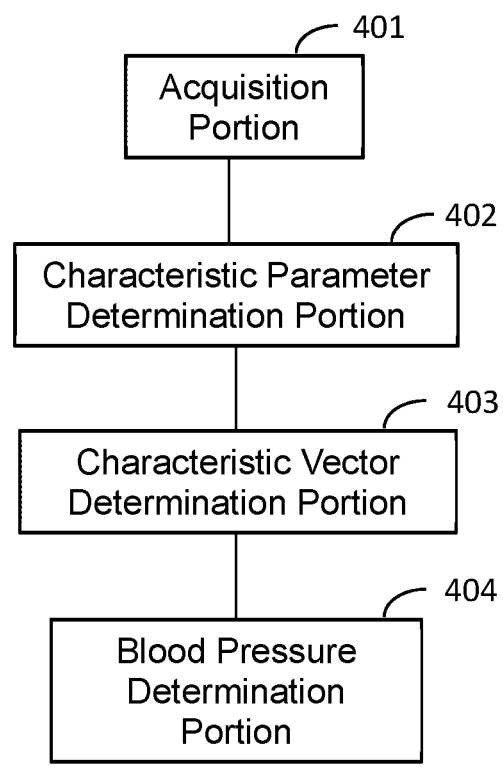
FIG. 6A illustrates an apparatus for determining a blood pressure of a user according to some embodiments of the present disclosure.

FIG. 6A illustrates an apparatus for determining a blood pressure of a user according to some embodiments of the disclosure. As shown in FIG. 6, the apparatus comprises an acquisition portion 401, a characteristic parameter determination portion 402, a characteristic vector determination portion 403, and a blood pressure determination portion 404.

The acquisition portion 401 is configured to collect a pulse wave signal and an ECG signal of the user;

The characteristic parameter determination portion 402 is configured to extract characteristic parameters of the user based on the pulse wave signal and the ECG signal collected by the acquisition portion 401;

The characteristic vector determination portion 403 is configured to establish a characteristic vector of the user based on the characteristic parameters of the user extracted by the characteristic parameter determination portion 402 and pre-determined personal information of the user; and The blood pressure determination portion 404 is configured to determine a blood pressure of the user based on the characteristic vector of the user established by the characteristic vector determination portion 403 and a pre-established characteristic-vector-and-blood-pressure relational model.

In the apparatus as described above, the characteristic parameter determination portion 402 is specifically configured to extract the characteristic parameters of the user from the ECG signal and the pulse wave signal of the user, wherein the characteristic parameters comprise a heart rate, a pulse wave transmit time, a pulse wave rise time, a pulse wave fall time, and a pulse wave peak value and a pulse wave trough value of two adjacent repeat cycles.

In the apparatus as described above, the pre-determined personal information comprises gender, age, height, and weight. The acquisition portion in the acquisition device can comprise an ECG signal collection sub-portion and a pulse wave signal collection sub-portion, which are respectively configured to collect an ECG signal and a pulse wave signal of the user.

It is noted that in the above mentioned apparatus for determining a blood pressure of a user, these above portions, including the acquisition portion 401, the characteristic parameter determination portion 402, the characteristic vector determination portion 403, and the blood pressure determination portion 404, are all functional portions/functional modules, and can be integrated into one or multiple devices in different combinations.

Figure 6B:
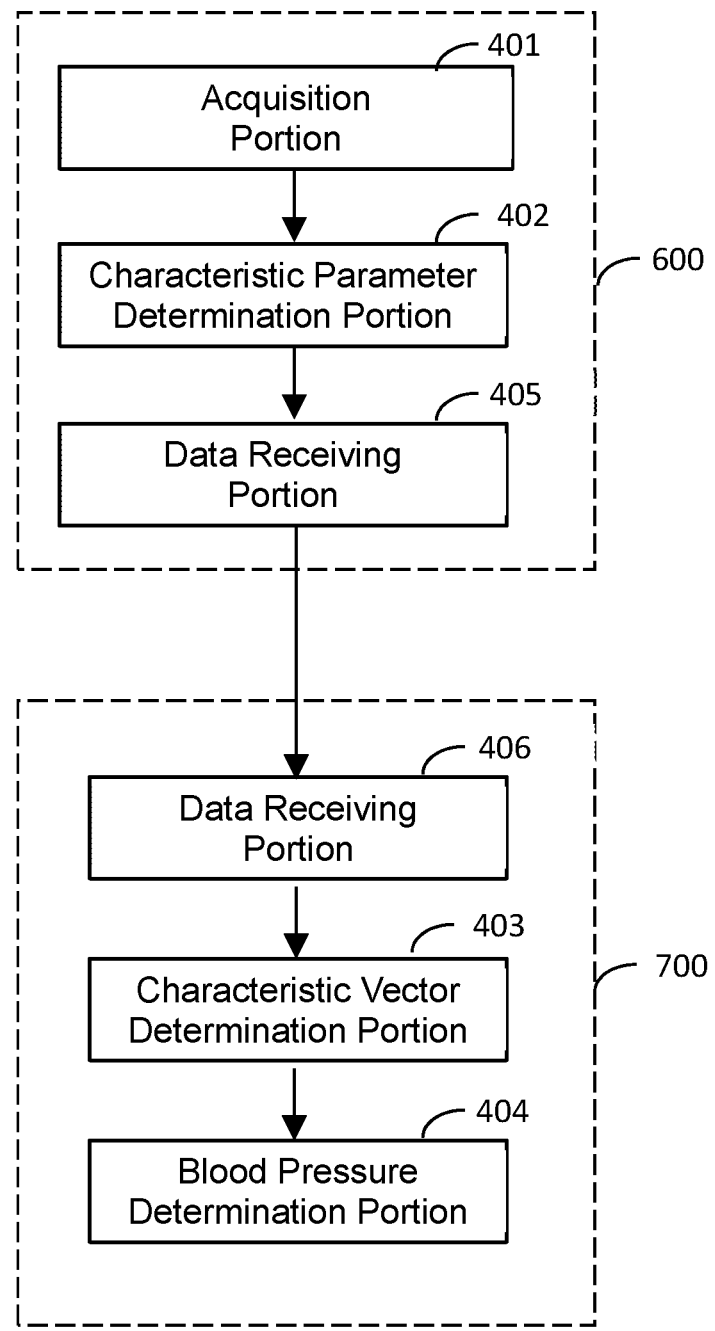
FIG. 6B is an apparatus for determining a blood pressure of a user according to some embodiments of the present disclosure.
Figure 7:
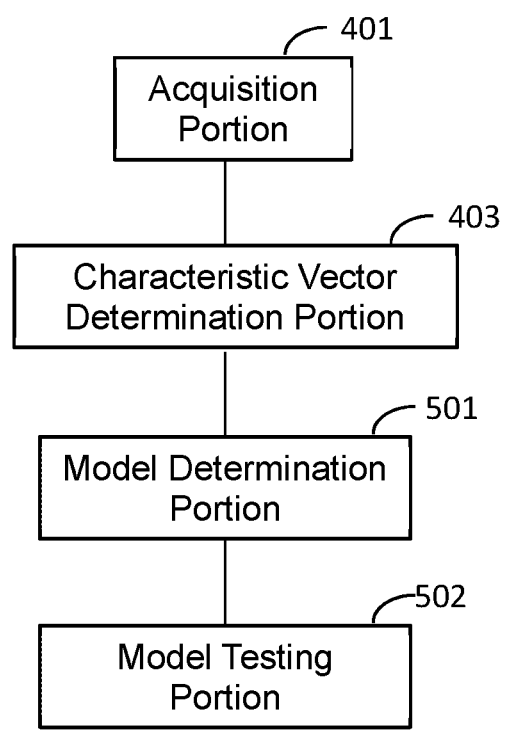
FIG. 7 shows a device for determining a blood pressure of a user according to some other embodiments of the present disclosure.

In one preferred embodiment of the apparatus, as show in FIG. 6B, the acquisition portion 401 and the characteristic parameter determination portion 402 are both integrated into an acquisition device 600, and the other two portions (i.e., the characteristic vector determination portion 403, and the blood pressure determination portion 404) are both integrated in a computing device 700. The acquisition device 600 is coupled to the computing device 700, and is configured to transmit the characteristic parameters of the user that have been extracted from the ECG signal and the pulse wave signal to the computing device 700.

Herein, the acquisition device 600 can be a wearable device (e.g. a smart bracelet), equipped with an ECG signal collection circuit, a pulse wave signal collection circuit, and a data processor, which are respectively configured to collect the ECG signal of the user (via the ECG signal collection sub-portion of the acquisition portion 401), to collect the pulse wave signal of the user (via the pulse wave signal collection sub-portion of the acquisition portion 401), and to extract the characteristic parameters of the user from the ECG signal and the pulse wave signal that have been collected by the ECG signal collection circuit and the pulse wave signal collection circuit (via the characteristic parameter determination portion 402), respectively. The data processor can be a SCM chip, but can be other types of chips.

The acquisition device 600 can also comprise a data transmission portion 405, which is configured to transmit the characteristic parameters of the user to the computing device. Herein the data transmission circuit is configured to perform data transmission via a wired transmission or a wireless transmission. Herein the wireless transmission can be through cellular, Wi-Fi, or preferably Bluetooth.

The computing device 700 can be a smart phone (e.g. smart phone), a computer, a remote server (e.g., a cloud server), and is configured to receive the characteristic parameters of the user from the acquisition device (via a data receiving portion 406), to establish a characteristic vector of the user based on the characteristic parameters of the user and pre-determined personal information of the user (via the characteristic vector determination portion 403), and to determine a blood pressure of the user based on the characteristic vector of the user and a pre-established characteristic-vector-and-blood-pressure relational model (via the blood pressure determination portion 404).

In another embodiment of the apparatus, only the acquisition portion 401 is integrated into an acquisition device, and the other three portions of the apparatus (i.e., the characteristic parameter determination portion 402, the characteristic vector determination portion 403, and the blood pressure determination portion 404) are all in a computing device.

In yet another embodiment of the apparatus, all four portions (i.e. the acquisition portion 401, the characteristic parameter determination portion 402, the characteristic vector determination portion 403, and the blood pressure determination portion 404) are all in a single device.

In addition to its use for determining a blood pressure of a user, the apparatus for determining a blood pressure of a user as described above can also be employed to establish the characteristic-vector-and-blood-pressure relational model.

According to some embodiments of the apparatus, the acquisition portion 401 is further configured to measure a pulse wave signal, an ECG signal, and a blood pressure of each of a plurality of sample individuals at each of a plurality of time intervals.

The characteristic vector determination portion 403 is further configured, after extracting characteristic parameters of each sample individual at each time interval from the ECG signal and the pulse wave signal thereof, to establish a characteristic vector of the each sample individual based on the characteristic parameters and pre-determined personal information of the each sample individual.

The apparatus further comprises a model determination portion 501, configured to determine a characteristic-vector-and-blood-pressure relational model based on the characteristic vector and corresponding blood pressure of a first sub-population of sample individuals.

In the apparatus as described above, the model determination portion 501 is specifically configured to determine the characteristic-vector-and-blood-pressure relational model based on the formula:

$$y = \sum_{i=1}^{l} (\alpha_i - \alpha_i^*)K(x, x_i) + b$$

where y is the blood pressure, l is the number of the characteristic vector of a sub-population of the sample individuals, $K(x,x_i)$ is the kernel function, x is the characteristic vector of a user, $x_i$ is the characteristic vector of the sub-population of the sample individuals, $\alpha_i$, $\alpha_i^*$, b are the optimal coefficients for each parameter after training.

The apparatus can further comprise a model testing portion 502, which is configured, after a characteristic-vector-and-blood-pressure relational model is determined, to obtain a calculated blood pressure of a second sub-population of the sample individuals based on the characteristic-vector-and-blood-pressure relational model and the characteristic vector of the second sub-population of the sample individuals, and if a difference between the calculated blood pressure and the measured blood pressure of the second sub-population of the sample individuals does not satisfy a preset standard, to re-determine the characteristic-vector-and-blood-pressure relational model until the preset standard is met.

In the above mentioned method and apparatus for determining a blood pressure of a user, the blood pressure of a user can be determined based on a characteristic vector of the user and a pre-established characteristic-vector-and-blood-pressure relational model, realizing a cuff-less measurement of the blood pressure.

Additionally, the characteristic vector of the user includes the personal information of the user and the characteristic parameters of the user that are determined based on the ECG signal and the pulse wave signal of the user. As such, during the process of blood pressure measurement, there is no need to calibrate for each individual person, bringing about convenience for use.

Furthermore, because the blood pressure of the user is determined based on both the ECG signal and the pulse wave signal, the measurement result is thus more accurate than the result obtained from a conventional measurement approach, where only the pulse wave signal is based to obtain the blood pressure.

Various modifications of, and equivalent acts corresponding to, the disclosed aspects of the exemplary embodiments, in addition to those described Although specific embodiments have been described above in detail, the description is merely for purposes of illustration. It should be appreciated, therefore, that many aspects described above are not intended as required or essential elements unless explicitly stated otherwise.

The invention claimed is:

1. An apparatus for determining a blood pressure of a user, comprising:
    an acquisition portion, configured to collect a pulse wave signal and an ECG signal including a heart rate, a pulse wave transmit time, a pulse wave rise time, a pulse wave fall time, and a pulse wave peak value and a pulse wave trough value of two adjacent repeat cycles from the user;
    a characteristic parameter determination portion, configured to extract characteristic parameters of the user corresponding respectively to the pulse wave signal and the ECG signal including the heart rate, the pulse wave transmit time, the pulse wave rise time, the pulse wave fall time, and the pulse wave peak value and the pulse wave trough value of two adjacent repeat cycles;
    a characteristic vector determination portion, configured to establish a characteristic vector of the user based on the characteristic parameters of the user extracted by the characteristic parameter determination portion and personal information of the user including gender, age, height, and weight of the user; and
    a blood pressure determination portion, configured to determine the blood pressure of the user based on the characteristic vector of the user established by the characteristic vector determination portion and a characteristic-vector-and-blood-pressure relational model;
    wherein the characteristic-vector-and-blood-pressure relational model is pre-established based on characteristic vectors and corresponding blood pressures of a first sub-population of sample individuals;
    the apparatus further comprising a model testing portion, wherein:

the model testing portion is configured, after the characteristic-vector-and-blood-pressure relational model is determined:
to obtain a calculated blood pressure of a second sub-population of the sample individuals, the second sub-population of the sample individuals being different from the first sub-population of the sample individuals and for testing of optimal coefficients of each parameter in the characteristic-vector-and-blood-pressure relational model, the calculated blood pressure of the second sub-population being based on the characteristic-vector-and-blood-pressure relational model and the characteristic vector of the second sub-population of the sample individuals; and
upon determination by the apparatus that a difference between the calculated blood pressure and the determined blood pressure of the second sub-population of the sample individuals does not satisfy a standard, the apparatus re-determines the characteristic-vector-and-blood-pressure relational model until the standard is met; and
wherein upon the difference satisfies the standard, the apparatus determines the characteristic-vector-and-blood-pressure relational model.

2. The apparatus of claim 1, wherein:
the acquisition portion and the characteristic parameter determination portion are arranged in an acquisition device;
the characteristic vector determination portion and the blood pressure determination portion are arranged in a computing device; and
the acquisition device is configured to send the characteristic parameters of the user to the computing device.

3. The apparatus of claim 2, wherein the acquisition device is a wearable smart device.

4. The apparatus of claim 2, wherein the computing device comprises one of a smart phone, a computer, or a remote server.

5. The apparatus of claim 2, wherein the acquisition device is configured to send the characteristic parameters of the user to the computing device via a wireless communication, selected from one of a cellular communication, a Bluetooth communication, and a Wi-Fi communication.

6. The apparatus of claim 1, further comprising a model determination portion, wherein:
the model determination portion is configured to determine a characteristic-vector-and-blood-pressure relational model based on the characteristic vector and corresponding blood pressure of a first sub-population of sample individuals;
the acquisition portion is further configured to measure a pulse wave signal, an ECG signal, and a blood pressure of each of a plurality of sample individuals at each of a plurality of time intervals; and
the characteristic vector determination portion is further configured, after extracting characteristic parameters of each sample individual at each time interval from the ECG signal and the pulse wave signal thereof, to establish a characteristic vector of the each sample individual based on the characteristic parameters and pre-determined personal information of the each sample individual.

7. The apparatus of claim 1, wherein the pre-established characteristic-vector-blood-pressure relation model is established via a support vector machine algorithm.

8. The apparatus of claim 1, wherein the characteristic-vector-and-blood-pressure relational model allows the apparatus to determine the blood pressure of the user without individual calibration for the user.

9. The apparatus of claim 1, wherein the apparatus is a cuff-less blood pressure measurement apparatus based on the characteristic vector of the user and the pre-established characteristic-vector-and-blood-pressure relational model.

10. The apparatus of claim 9, wherein the characteristic vector of the user includes personal information of the user and characteristic parameters of the user that are determined based on the ECG signal and the pulse wave signal of the user, and the apparatus is configured to obtain the blood pressure of the user without individual calibration for the user.

11. The apparatus of claim 10, wherein the first sub-population are configured for the determination of the characteristic-vector-and-blood-pressure relational model, and the second sub-population are configured for testing of the optimal coefficients of each parameter in the relational model that have been determined.

12. The apparatus of claim 11, wherein the standard is set as within ±5 mmHg for an average of differences, or <12 mmHg of a standard deviation, and an accuracy of the relational model is determined by an average or a standard deviation of a difference between a calculated blood pressure based on the second sub-population and the measured blood pressure.

13. The apparatus of claim 12, wherein upon a testing result meeting the standard, the apparatus is configured to output the characteristic-vector-and-blood-pressure relational model as characteristic-vector-and-blood-pressure relational model for subsequent determination of a blood pressure of a user.

14. The apparatus of claim 13, wherein the apparatus is configured to determine the characteristic-vector-and-blood-pressure relational model based on:

$$y = \sum_{i=1}^{l} (\alpha_i - \alpha_i^*)K(x, x_i) + b,$$

where y is the blood pressure, l is number of the characteristic vector of a sub-population of the sample individuals, $K(x,x_i)$ is a kernel function, x is the characteristic vector of the user, $x_i$ is the characteristic vector of the sub-population of the sample individuals, $\alpha_i$, $\alpha_i^*$, b are the optimal coefficients for each parameter after training.

* * * * *